United States Patent [19]
Berkeley

[11] 4,080,962
[45] Mar. 28, 1978

[54] POSTURE-TRAINING BRACE

[76] Inventor: Joseph Berkeley, 1273 Ouellette Ave., Windsor, Ontario, Canada, N8X 1V3

[21] Appl. No.: 598,673

[22] Filed: Jul. 24, 1975

[51] Int. Cl.² ............................................. A61F 5/02
[52] U.S. Cl. .......................................... 128/78; 2/44
[58] Field of Search ............... 128/78, 87 R, 83; 2/44, 2/45

[56] References Cited
U.S. PATENT DOCUMENTS

| 10,248 | 11/1853 | Browne | 128/78 X |
| 1,931,990 | 10/1933 | Massack | 128/78 |
| 2,541,487 | 2/1951 | Triplett | 128/78 |
| 3,771,513 | 11/1973 | Velazquez | 128/78 |

FOREIGN PATENT DOCUMENTS 1,104,562  11/1955  France .................. 128/78

Primary Examiner—John D. Yasko
Attorney, Agent, or Firm—Ridout & Maybee

[57] ABSTRACT

A brace for posture training comprises a thoracic band, a pelvic band resting on the base of the sacrum and arched over the hip joints and beneath the front of the hip bone, and resilient struts extending between the bands so as resiliently to oppose undesirable changes in posture.

9 Claims, 3 Drawing Figures

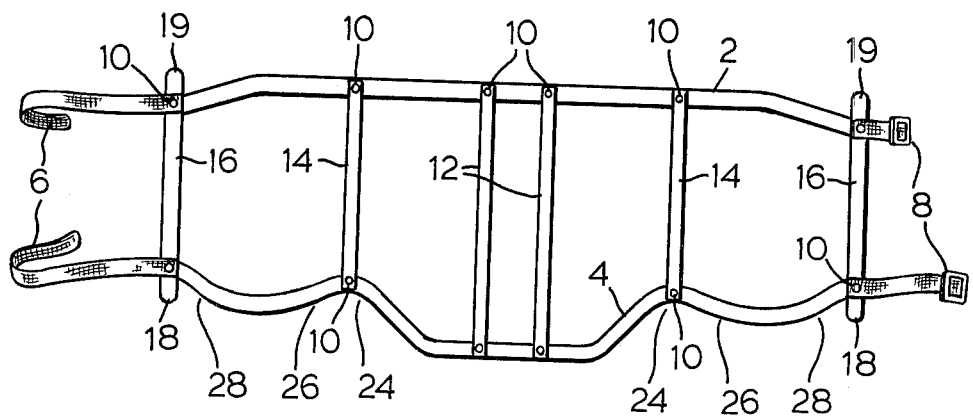
FIG 1
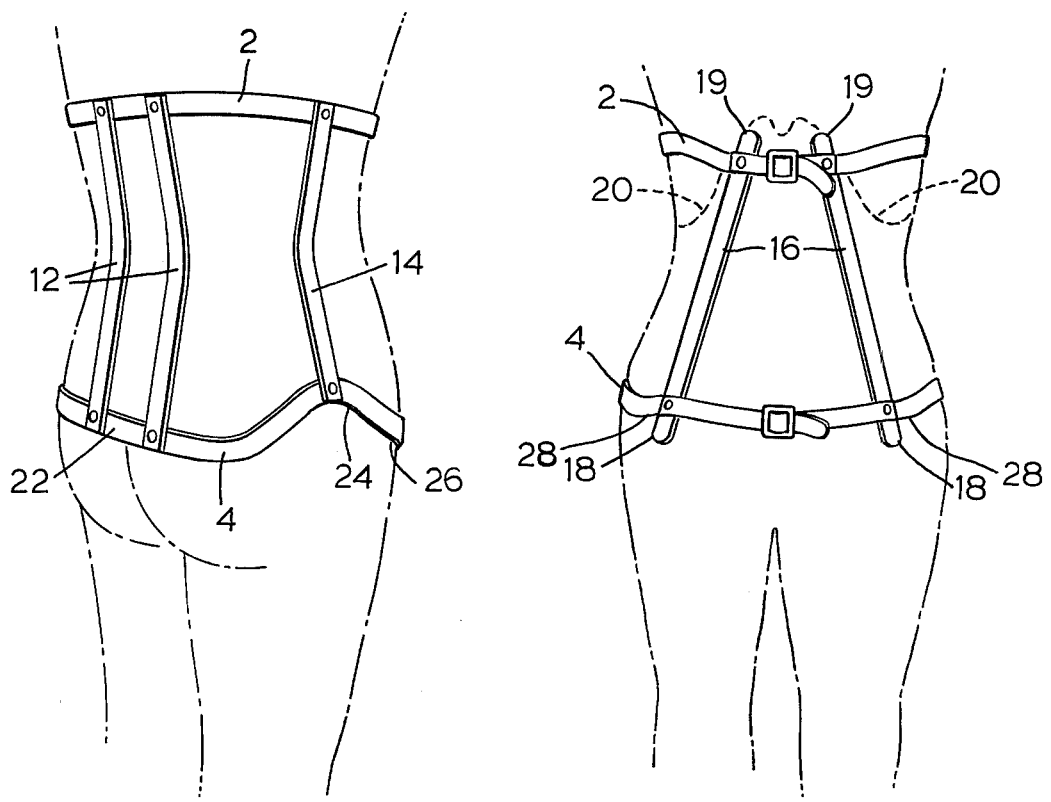
FIG. 2
FIG. 3

POSTURE-TRAINING BRACE

FIELD OF THE INVENTION

This invention relates to back braces for posture training purposes, and more particularly braces for the purpose of training a patient to maintain a straight back in different postures and during different movements.

REVIEW OF THE PRIOR ART

A brace of the type which the invention is directed should desirably have various characteristics. It should inhibit undesirable spinal movement. It should not cause disuse and therefore deconditioning of the patient's muscles. It should not obstruct normal activities and postures such as walking and sitting, and ideally it should be possible to wear it even while swimming, exercising or bathing in a swimming pool or in the sea. It should be of open work construction so as to provide good ventilation of the patient's trunk and minimum discomfort during wear. It should be simple to fabricate and fit to the patient, and to modify should the patient change in weight or shape. It should encourage the patient to adopt correct postures.

Numerous types of brace have been proposed or actually used, but it is not believed that any of these succeed in fulfilling all of the above requirements.

A common feature of nearly all belts in common use is the use of either an apron or a number of straps crossing the abdomen, with the dual purpose of applying pressure to the abdomen and providing the necessary support for the portion of the device which engages the back. This arrangement is thought to have the advantage that it increases the intra-abdominal pressure, and by doing so relieves part of the load on the patient's spine, but has the disadvantage that it tends to lead to the disuse of the abdominal muscles and resulting undesirable weakness. Moreover, the pad or apron can be a source of discomfort, and is unacceptable for use when pressure on the abdomen must be avoided, as during pregnancy, or where patients suffer from pain in the region of the stomach and gall bladder and cannot tolerate strong pressure.

Moreover, in general, known braces tend to seek to immobilize the patient's back, which again leads to problems due to muscular disuse and consequent weakness. Furthermore, most known braces, whilst successful in restraining certain types of undesirable movement by the patient, fail to restrain other undesirable movements. Thus, for example, a particular brace may exercise adequate control over rearward and sideways bending, but little or no control over forward bending.

Finally, since most known braces seek to operate by immobilizing the back, they are effective only so long as they are worn and do little towards training the patient to adopt desirable postures as a habit. In fact they may even hinder such adoption by weakening the muscles required to maintain such postures.

SUMMARY OF THE INVENTION

The present invention seeks to provide a back brace which progressively discourages rather than positively prevents undesirable postures, which does not cause any group of muscles to become disused, which is effective to inhibit undesirable bending movements in any direction, and which does not require the abdomen to be covered or subjected to pressure. The brace does not interfere with normal walking or sitting movements, is simple in construction and is easy to fit to the patient.

A posture training back brace according to the invention comprises a semi rigid thoracic band adapted to surround the back and sides of the rib cage of a patient with the front ends of the band curved around to cross the front margins of the rib cage, a semi rigid pelvic band adapted to surround the back and sides of the pelvis of a patient with the rear portion of the band seated on the lower end of the sacrum, the side portions of the band being arched upwardly from the rear portion to clear the hip joints of the patient, with the front ends of the band curved around to pass beneath the front of the hip bones, tensioning straps connecting the front end of each of the bands, and a plurality of resiliently flexible struts extending between the bands. Preferably also, short downwardly projecting spurs are provided at the front ends of the pelvic band disposed so as to extend towards the groins of the patient, short upwardly projecting spurs are provided at the front ends of the thoracic band disposed so as to extend towards the rib margin or breastbone of the patient, the side portions of the pelvic band are curved downwardly and then upwardly in front of the hip joint so as to fit better beneath the hip bone without obstructing movement of the thighs, and the struts are located dorsally to either side of the spine, ventrally to either side of the abdomen, and laterally above each hip joint, at least the dorsal and lateral struts comprising highly resilient material such as spring steel. Conveniently, the upwardly and downwardly projecting spurs are formed by extensions of the ventral struts.

With the brace of the invention, bending movements of the back are resisted rather than positively prevented, any such movement in any direction resulting in flexing and inward arching of at least some of the flexible struts, with a progressively increasing resistance to the movement, excessive movement also resulting in some part of the brace bearing into the patient to provide a reminder that the movement is impermissible. Thus not only are undesirable movements inhibited, but by reason of the pressure and discomfort feedback provided by the brace, the patient learns to avoid such movements automatically. In practice, the restriction on movement over the first 10–15% of any possible bending movement is only slight, and such permitted movement avoids the danger of muscular weakness due to disuse. Moreover, the flexibility of the struts permits a degree of relative rotation between the bands, thus allowing for a normal degree of hip rotation during walking whilst resisting excessive twisting movements of the spine. The brace is of open work construction and no part of it need bear on the abdomen in any way, thus permitting use of the brace during pregnancy and avoiding weakening of the abdominal muscles. Indeed, for just so long as the patient only adopts permissible postures, the brace has little or no effect and is therefore unlikely to have any harmful influence.

The thoracic and pelvic bands may be formed by heating strips of thermoplastic material which are moulded under the influence of heat so as to assume an appropriate relationship to the shape of the patient's body. The shape of the brace may readily be adjusted by the same means should weight loss by the patient necessitate this. The struts may be formed of spring steel strip and riveted to the bands.

The invention is described further with reference to the accompanying drawing, in which:

FIG. 1 is a view of a brace in accordance with the invention, laid out flat;

FIG. 2 is a view from the rear and one side of a patient wearing the brace, and

FIG. 3 is a corresponding view from the front and the other side.

A general view of a typical brace is shown in FIG. 1 in flat form prior to fitting to a patient. Its construction is very simple, there being a thoracic band 2, a pelvic band 4, tensioning straps having strap and buckle portions 6 and 8, and spacer struts secured between the bands 2 and 4 by rivets 10, the struts comprising two dorsal struts 12, two lateral struts 14, and two ventral struts 16.

The bands 2 and 4 are formed of semi rigid thermoplastic strip material, such as polyethylene, polypropylene or polyvinyl chloride. By semi rigid I mean that the material has sufficient rigidity to provide a firm support for the spacer struts, but sufficient flexibility to permit the brace to be placed upon and removed from the patient during normal use, as described further below.

The struts 12 and 14 are preferably formed by resilient strips of spring steel, whilst the struts 16 may be of the same thermoplastic strip material as the bands 2 and 4. The struts 12 and 14 may also if desired be of thermoplastic strip material, reinforced by spring steel strips. In some cases, additional reinforcement of the dorsal struts may be necessary, for example by adding additional spring steel strips of appropriate thickness to resist rearward bending movements by certain muscular or heavily built patients. The strap portions 6 and 8 may be formed of webbing or flexible synthetic plastic material, provided with appropriate buckles or other fastenings to enable the bands to be secured around the body of a patient.

In order to fit the brace to a patient, the assembly so far described is constructed to dimensions in accordance with measurements taken from the patient, and the material of the bands 2 and 4 and the struts 16 is heated sufficiently to render it plastic, whereupon the brace is fitted to the patient and the bands and struts moulded so as to lie against the surface of the body in correct positions. This fitting is illustrated further in FIGS. 2 and 3.

It will be seen that the thoracic band 2 passes around the back and sides of the rib cage of the patient, the front ends of the band being turned inwardly to pass across the margins of the rib cage (shown in broken lines at 20), and the strap connecting them passes beneath the breast bone.

The pelvic band 4 is formed so that a portion 22 rests at the rear of the patient, against the lower end of the sacrum as shown in FIG. 2. At the patient's sides, the band bends upwardly so as to arch over the hip joint at 24 with sufficient clearance to allow normal operation of the leg muscles, and then in a preferred configuration curves down at 26 to pass beneath the front protuberance or spine of the hip or iliac bone and then upwardly at 28 sufficiently to allow normal movement of the patient's thighs into a sitting position. The portions 26 and 28 may be more or less level, but this will generally provide a less comfortable fit relative to the pelvic bone structure. The inner ends of the band may have inward and downward projections 18 extending towards the patient's groins, although an alternative and preferred arrangement for providing these projections is described below. The strap connecting the ends of the band passes beneath the belly.

The struts are positioned so that the dorsal struts 12 lie to either side of the spine, the lateral struts 14 are located above the hip joints and ventral struts 16 lie to either side of the belly. It will be seen therefore that since the straps pass above and below the belly, and the struts 16 pass more or less to either side, there is no abdominal pressure or support provided by the brace. Even though the struts 16 may pass across the sides of the abdomen, there is no need for them to press against it during normal wear of the brace: the struts 16 may be moulded if required to provide additional space for the abdomen. The struts 16 preferably project at their top and bottom ends beyond the thoracic and pelvic bands, the extent of these projections 18 and 19 being such that when the patient's back is unbent, the top and bottom ends of the strut fall sufficiently short of the rib margin or breast bone and the groin respectively to avoid discomfort to the patient, and to avoid the brace riding up on the patient's body during sitting or permissible bending movements.

Because of the shape of the human body, the bands 2 and 4 will tend to be inclined slightly inwardly towards one another, resulting in the struts 12, 14 and 16 assuming a slight inwardly concavity following the contours of the body. Moreover, because the waist is normally slimmer than the hips, the struts 16 will in such cases be inclined towards one another, as shown in FIG. 3.

Once the brace is fitted and the straps tightened so that the bands 2 and 4 are a snug fit around the patient, relative movements of the thorax and the pelvis, beyond a small degree accommodated by slight movement of the bands on the patient, will require distortion of at least some of the struts 12, 14 and 16, which distortion will be resisted by the resilience of the struts, the resistance increasing with the degree of movement. Moreover, the forces generated will tend to tilt the bands 2 and 4 relative to the body. Thus a forward bending movement will cause upward pressure to be applied to the front ends of the band 2, causing them to press against the rib margins at 20, and downward pressure to be applied to the front ends of the band 4. Forward bending beyond an extent determined by the length of the struts 16 will cause the projections 18 just to dig into the groins, and the projections 25 just to contact the rib cage, the resulting discomfort providing a reminder that the movement is impermissible and training the patient to avoid such movements. A bend to the front and one side results in a similar effect on the side concerned, and in addition the lateral strut 14 on the side concerned will fold inwardly and press against the top of the hip bone. Excessive twisting of the body will again cause the front ends of the band 2 to bear on the rib margin.

Because the rear of the pelvic band is supported on the base of the sacrum well below the lumbo-sacral hinge, rearward bending movements will result in pressure being applied to the sacrum. Other impermissible bending movements may pull the front ends of the band 4 upwards against the front end of the hip bone. In effect, the brace will rest comfortably against the body until an impermissible bending movement of the spine is attempted, whereupon it will begin to resist that movement and will also apply pressure to the patient at some point where a margin of the bone structure is close to the surface of the body, so as to inhibit further movement. The patient is thus reminded and in time trained to avoid undesirable movement without the necessity for actual immobilization.

The location of the pelvic band, and the normal lack of interaction between the body and the various struts, overcomes a common problem of back braces, that of the brace riding up on the body as the patient bends or sits, without the necessity of providing groin straps or the like to hold it down. Any tendency to riding up which does appear normally occurs because the projections 18 have been made too long, and this can readily be corrected merely by shortening the bottom ends of the struts 16 with a pair of snips.

In most cases it will be found that the brace can be made in a few standard sizes, for example small, medium and large, and fitting then merely involves selecting the appropriate size, moulding the heat-softened bands 2 and 4 to the contours of the body, and adjusting the ventral struts 16, both as to their points of attachment to the bands 2 and 4, according to the waist length of the patient, and as to the distances by which the ends of the strut project beyond the bands to form the projections 18 and 19. The struts 16 may also be moulded if required to provide additional clearance for the abdomen.

The nature of the construction of the brace means that it is easily and cheaply constructed, fitted or modified without the exercise of any exceptional degree of mechanical skill, it is cool, light and hygenic to wear, and it interferes to a minimum degree with the normal clothing and activities of the patient.

What I claim is:

1. A posture training back brace comprising a semi rigid thoracic band adapted to surround the back and sides of the rib cage of a patient with the front ends of the band curved around to cross the front edges of the rib cage, a semi rigid pelvic band adapted to surround the back and sides of the pelvis of a patient with the rear portion of the band adapted to be seated on the lower end of the sacrum, the side portions of the band being arched upwardly from the rear portion to clear the hip joints of the patient, with the front ends of the band curved around to pass beneath the front protuberance or spine of the hip or iliac bones, tensioning straps connecting the front ends of each of the bands and a plurality of resiliently flexible struts each extending between the pelvic band and the thoracic band, these struts including inwardly arched struts adapted to be located dorsally to either side of the spine, further inwardly arched struts adapted to be located laterally above each hip joint, and additional struts adapted to be located ventrally to either side of the abdomen.

2. A brace according to claim 1, including, at the front ends of the pelvic band, short downwardly directed projections extending towards the groins of the patient.

3. A brace according to claim 2, including, at the front ends of the thoracic band, short upwardly directed projections extending towards the breastbone of the patient.

4. A brace according to claim 3, wherein the upwardly and downwardly directed projections are formed by the ends of struts extending between the two bands at the front ends thereof.

5. A brace according to claim 1, wherein the side portions of the pelvic band are curved downwardly and then upwardly in front of the hip joint so as to fit better beneath the front protuberance of the hip bone without obstructing movement of the thighs.

6. A brace according to claim 1, wherein the dorsal and lateral struts are of spring steel strip.

7. A brace according to claim 1, wherein the ventral struts are of resilient thermoplastic material.

8. A brace according to claim 7, wherein the ventral struts project a short distance beyond the thoracic and pelvic bands.

9. A brace according to claim 1, wherein the thoracic and pelvic bands are formed from thermoplastic material.

* * * * *